Figure 1:
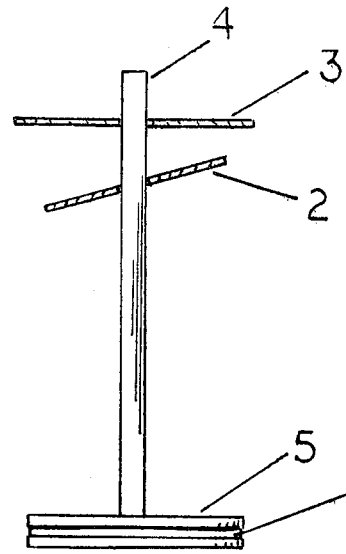
Figure 2:
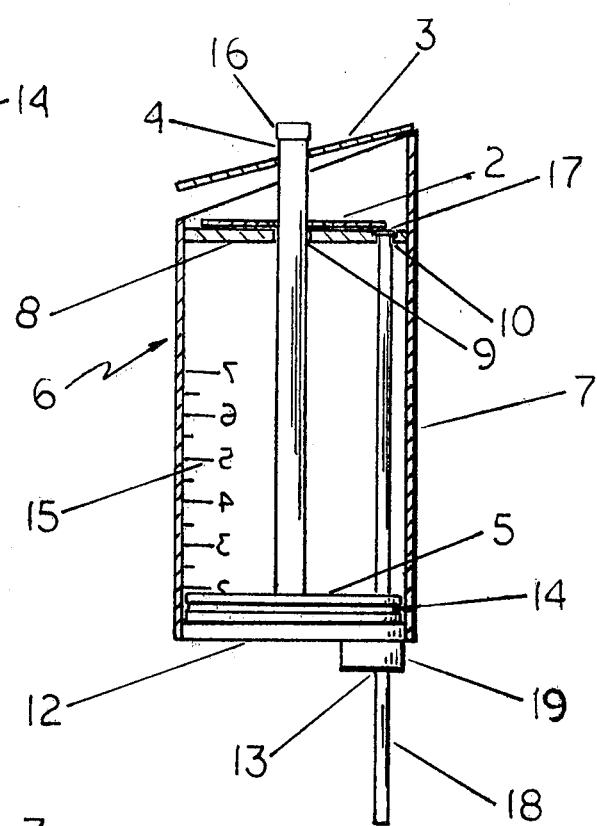
Figure 3:
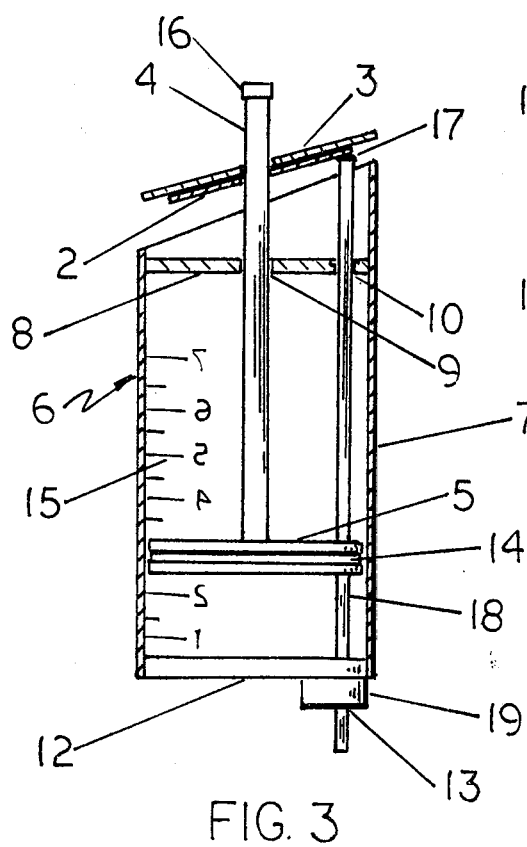

United States Patent [19]

Gereg et al.

[11] 4,347,853
[45] Sep. 7, 1982

[54] CYCLE COUNTER FOR LUNG EXERCISER

[75] Inventors: Gordon A. Gereg, 557-A Blue Church Rd., Coopersburg, Pa. 18036; Robert K. Rightler, Pennsburg, Pa.

[73] Assignee: Gordon A. Gereg, Woodbury, Conn.

[21] Appl. No.: 236,648

[22] Filed: Feb. 23, 1981

[51] Int. Cl.³ .............................................. A61B 5/08
[52] U.S. Cl. ................................... 128/725; 128/728; 235/87 R; 235/1 B; 272/99; 116/225; 116/283
[58] Field of Search ............... 128/716, 721, 725, 727, 128/728, 729, 205.23; 272/99; 116/200, 283, 281, 225; 235/1 B, 87 R, 87 A

[56] References Cited
U.S. PATENT DOCUMENTS

| 276,101 | 4/1883 | Wales | 235/1 B |
|---|---|---|---|
| 1,278,315 | 9/1918 | Drake | 235/87 R |
| 3,559,639 | 2/1971 | Nagus | 128/728 |
| 3,669,097 | 6/1972 | Fitz | 128/728 |
| 3,754,546 | 8/1973 | Cooper | 128/728 |
| 3,822,699 | 7/1974 | Cleary | 128/727 |
| 3,862,628 | 1/1975 | Williams | 128/727 |
| 3,871,364 | 3/1975 | Boehringer | 128/727 |

FOREIGN PATENT DOCUMENTS 612126 11/1948 United Kingdom ............... 128/727

Primary Examiner—Henry J. Recla

[57] ABSTRACT

A simple device intended to register the number of cycles performed by a patient using a lung exerciser. A means for easily resetting to zero is provided. The device is adaptive to various sizes, scales, and maximum number of cycles.

2 Claims, 3 Drawing Figures

U.S. Patent  Sep. 7, 1982  4,347,853

CYCLE COUNTER FOR LUNG EXERCISER

FIELD OF INVENTION

Registers

RELATED APPLICATION

This device would work particularly well with a lung exerciser as described in pending patent application No. 06/199,084 of Gordon A. Gereg. A lung exerciser including the one in the prior application can function without a counter but the convenience and utility is improved with the device in use. The counter would work equally well with a number of different lung exerciser designs provided an adaptation means was present.

OBJECTS

Patients with severe illness or those having been operated on often are weak to the point they find it difficult to breath deeply. The human lung is a labyrinth of passages that get increasingly smaller deeper into the lung. If the small passages are not used at least occasionally over a period of time they tend to clog and could atrophy. A normally healthy person will sigh or yawn on a fairly regular basis which exercises the small passages of the lungs. Deep breathing exercises or activities that require heavy breathing such as running are good for the lungs.

Since lung problems with inactive patients are a well known phenomenon, therapists have for some time used various devices to get the patient to use or redevelop their lungs. Among these are blow bottles which require a patient to blow water out of a bottle; ball type flowmeters which force a patient to draw or expire breath at a higher than normal rate; and volume related devices that measure the vital capacity of the lung and encourage deep breathing. There are also a number of positive pressure devices which force pressure into the lung to expand it with the patient being passive.

The volume related devices that require a patient to inhale a set amount of air and repeat the exercise a number of times are the most popular currently. Generally they are a collapsible container with graduated volume that the patient must inhale 10 to 20 times a treatment. Bellows are commonly used as are folding bags and boxes. It is important that the container offer as little resistance as possible when being emptied since it is the volume inhaled that is important and not the force needed to do it. A counter used in conjunction with a bellows device must take very little force to actuate since the only force available comes from contact with the bottom of the bellows and the patient is at the limit of his energy when the bellows is fully evacuated.

A variety of registers are available that could count cycles of a lung exerciser. Most are expensive such as electronic means and many need considerable force to actuate their mechanism. The device proposed can be sized and calibrated ideally to the use intended rather than being an adaptation of a counter designed for other uses. The needs of patient care environment are considered in ruggedness and simplicity. A signal apparatus is also unique and is used to tell the patient he has reached his goal of drawing the volume prescribed into his lungs.

What is proposed here is a simple, inexpensive device that can be readily understood and used and can be thrown away after one patient uses it. The design allows for freedom in setting the number of cycles that can be counted and the spacing of the graduations. Adaptors for use with various available lung exercisers are easily provided.

A simple counter can be made using an escapement based on jam washers. If a rod has on a washer having a bore slightly larger than the rod diameter, the washer will slide freely if it is at a right angle to the rod axis. Cocking the washer slightly will cause the washer to jam and grip the rod rather than slide along it. After the washer is jammed the rod will then move with any push on the washer parallel to the axis of the rod. The jam action is only in one direction, as soon as the jamming force is removed, the washer will loosen its grip. To make an escapement, two jam washers on the same rod are needed with different jamming forces. By alternating which washer grips the rod, the position of the rod will be related to the relative movement of the washers.

Considering a rod two washers are on to be vertical, the washers would be free to move up or down when they were horizontal or at right angles to the rod axis. If one washer had a larger outer diameter it could be forced into a jamming mode by a force farther from the rod axis than for a smaller diameter washer. By using two different outer diameter washers the escapement action can be accomplished by alternately forcing one or the other washer on a common vertical rod with parallel forces from below the washers.

The vertical rod the washers act upon can be set in two bearings to hold it vertical while letting it slide up and down. A preferred embodiment would use one bearing installed in a cylinder larger than the smaller jam washer and have the other bearing take the form of an enlargement of the vertical rod so it could be guided by the inner diameter of the cylinder. Both bearings are essentially simple discs with one having a clearance fitting bearing hole at its center and being pressed into a cylinder by its outer diameter and one having a press fit hole at the center and a clearance fit of its outer diameter to the same cylinder. When assembled, the rod with a disc pressed on one end and the other end clearance fitted into a bearing; said bearing being pressed into a cylindrical tube, can move up and down relative to the cylinder.

If both jam washers are put on the bearing rod above the bearings a means for forcing the washers up from below the assembly can be provided by drilling a hole parallel to the bearing rod running through both bearings discs and being at a radius from the bearing rod less than the radius of the smaller washer. A second rod installed through these aligned holes can be used to push up one side of the lower and smaller diameter jam washer causing it to move and jam, thereafter pushing the bearing rod assembled to the lower bearing with it.

The upper and larger diameter jam washer should be larger than the inner diameter of the cylinder. The upper end of cylinder where the washer would contact it should be cut at an angle so one side of the washer installed on the bearing rod would contact the high side of the cylinder first, causing the washer to cock and jam. The high point of the angle cut of the cylinder should be aligned with the guide holes cut through the bearings for the push rod.

When the lower jam washer is pushed from rest into the jamming mode and further pushed taking along the bearing rod assembly, it can be pushed a distance to contact the upper jam washer. The upper jam washer would be in the jammed mode at rest but an upward movement of the bearing would not be restricted, only a downward movement. Therefore, the bearing rod assembly would move up with the lower jam washer but would not fall back down with the lower jam washer because the upper jam would hold it up.

The amount of movement of the lower jam washer and bearing rod until the upper jam washer is contacted determines the distance the bearing rod assembly will travel with each stroke since once the washers are in contact both washers will move and both will fall back as an assembly with the bearing rod. The upper jam washer will stop the downward movement of the bearing rod each time it seats on the angled top of the cylinder tube. An alternative method of stopping the upper washer might be a protuberance on the wall of the tube or an extension of the upper bearing disc.

Since the lower bearing moves up with each stroke it is a logical place to mount or mark an indicator of movement. A corresponding scale on the cylinder wall could be used to count the total cycles assuming the cylinder wall was clear or a clear window could be provided so the lower bearing carrying a marker or indicator could be seen. A reading could be taken each time the assembly was at rest with the upper jam washer seated on the top of the cylindrical tube.

To complete the assembly a third disc with a guide hole should be pressed into the cylindrical tube at its lower end or as an alternative the tube could be closed on one end. This disc would have only a guide hole for the push rod, the hole being aligned with the guide hole in the other two bearing discs. The underside of the guide disc could be fitted with an adapter to allow the assembly to be fitted on another device such as a lung exerciser which has movement cycles needing counting. The push rod should extend out of the lower bearing disc and adaptor a sufficient amount to contact the moving part of its mating assembly. In any case the push rod must extend slightly more than the length of one stroke or the distance the lower jam washer must be moved before it contacts the upper washer. Extending the push rod in this manner assures the cycle can be completed before the push rod disappears into the adaptor.

For some applications a light actuating force is important and for this reason the weight of the moving parts should be minimized. Using tubing for the bearing and push rods and using plastic instead of metal parts as well as reducing the size of the parts, will reduce the force to cycle the counter.

The accuracy of the counter depends on the grip of the jam washers on the bearing rod. Having sharp edges on the hole in the washer will improve its grip as well as choosing materials properly. The bearing rod must be accurate in regard to diameter so the amount the washer must cock to grip the bearing rod remains constant along the length of the rod. Undercuts in the bearing rod could be used to define the stops for the washers. The diameter and length of the device can be varied to suit the number of cycles to be counted and the size of the scale to be used.

These and other objects will be apparent from the following drawings and specifications in which:

FIG. One shows a vertical cross sectional view of two jam washers on a rod with lower bearing disc attached.

FIG. Two is a vertical cross sectional view of an assembled counter in the lower, at rest state.

FIG. Three is a vertical cross sectional view of an assembled counter in an upper, active mode.

Referring now to the drawings in which like reference numerals denote similar elements, FIG. One shows a round rod 4 with one end press fitted into a flat circular disc 5. A large outer diameter washer 3 having a bore slightly larger than rod 4 is shown horizontal to rod 4 and free to slide up and down. A smaller outer diameter washer 2 is shown on rod 4 cocked at an angle which would cause the washer 2 to grip the rod 4 as long as a force was maintained to keep washer 2 at an angle to rod 4. The amount of gripping action is proportional to the force applied to washer 2. A washer in this specification is defined as a thin, flat circular disc having a hole at its center.

FIG. Two shows an assembled counter referred to generally as 6 in which a bearing disc 8 has been fitted a short distance into a thin walled cylindrical tube 7 near its upper end and fixed in place by suitable means such as glue. Said bearing disc 8 has a clearance hole 9 which would allow bearing rod 4 to slide freely when installed and another similar clearance hole 10 which would allow a push rod 18 to slide freely when installed. The bearing rod 4 with disc 5 attached can be easily slid up and down inside tube 7 since disc 5 has proper clearance at its outer diameter and rod 4 likewise has proper bearing clearance for free movement but sufficient guiding to keep the movement straight. With the bearing rod 4 and disc 5 inside the tube 7 a bottom guide disc 12 can be pressed or otherwise permanently fixed into the lower end of tube 7 and made flush to the end of tube 7 or tube 7 can be made with one closed end. Washer 2 can be simply dropped on bearing rod 4 and will seat itself in a rest position flat on bearing disc 8. Washer 3 can be dropped on bearing rod 4 and will seat itself on the top of tube 7 which has been cut at an angle larger than the angle washer 3 would assume if one side was forced as far as it would go making the washer 3 cock on bearing rod 4. In this manner washer 3 normally is locked to bearing rod 4 when at rest. Washer 3 could also alternatively be stopped by a protuberance of the wall of tube 7 or an extension from upper bearing disc 8.

Guide disc 12 is fitted into tube 7 at the end opposite the angle cut. This guide disc 12 has a clearance hole 13 for push rod 18; said hole being aligned with hole 10 in upper bearing disc 8. At the bottom of guide disc 12 an adaptor 19 may be provided to allow the assembly to be installed in working position with push rod 18 extended to receive pulses from some moving object.

In operation a small force on push rod 18 would move it up taking lower jam washer 2 up with it. When the lower jam washer 2 was forced into a small angle relative to bearing rod 4, it would lock on bearing rod 4 and any further upward movement of lower jam washer 2 would carry the assembly of push rod 2 and disc 5 up also. When the lower jam washer 2 was pushed far enough, it would contact upper jam washer 3 which would also be carried up with the bearing rod 4 once it was in contact with lower jam washer 2. FIG. Three shows the assembly in an upper mode. As the push rod 18 was let back down, the assembly of push rod 4 with indicator 5 and jam washer 2 and jam washer 3 would also travel down. Upper jam washer 3 would be stopped in its downward movement by contacting tube 7. Since tube 7 is cut at an angle, jam washer 3 would come to rest at an angle also. If the angle cut of tube 7 is properly set to be larger than the angle required to lock upper jam washer 3 to bearing rod 4, upper jam washer 3 will come to rest locked to bearing rod 4 with the higher side of jam washer 3 in contact with tube 7 and lower side clearing tube 7. Since upper jam washer 3 is locked to bearing rod 4, lower jam washer 2 will return to its unlocked position and slide freely back to rest. As lower jam washer 2 is returning to rest, bearing rod 4 is being held by upper jam washer 3.

Each time push rod 18 is pushed up the distance necessary to make lower jam washer 2 contact upper jam washer 3, bearing rod 4 and disc 5 will be advanced upward a distance proportional to the distance between the jam washers when both are locked to bearing rod 4. If the push rod 18 is advanced more than the distance necessary for a cycle, the entire assembly of bearing rod 4, disc 5, lower jam washer 2, and upper jam washer 3 will be carried upward in an override that will have no effect on the advance of the counting indication since the entire assembly will fall back the override distance with no relative motion of the parts of the assembly as the push rod 18 falls back.

A means for using disc 5 as an indicator or marker may be provided by a line 14 of contrasting color around its circumference in a band thinner than the width of disc 5. A corresponding scale of graduations 15 on the tube 7 assuming tube 7 was either transparent or had a slot cut in its side to allow disc 5 with line 14 to be seen, would allow the motion of disc 5 to be registered each time a cycle was completed. An extension of disc 5 could protrude through a slot in tube 7 if an exterior marker or pointer was desired.

The motion per cycle of disc 5 can be calibrated by sizing the clearance of lower jam washer 2 with bearing rod 4 and also by the spacing between lower jam washer 2 and upper jam washer 3. If the clearance of lower jam washer 2 is small relative to bearing rod 4, lower jam washer 2 will jam at a small angle to bearing rod 4 meaning it will engage or lock with a small amount of movement of push rod 18. The distance lower jam washer 2 travels while locked to bearing rod 4 and before upper jam washer 2 is contacted is the distance disc 5 with indicator line 14 will travel each upward cycle. Reducing the distance between lower jam washer 2 and upper jam washer 3 will bring the graduations 15 closer together and allow more cycles to be counted with a particular overall length of tube 7.

For the graduations to be equally spaced it would be necessary for bearing rod 4 to have a constant outer diameter. A relatively hard, stiff material such as metal or hard plastic should be used for lower jam washer 2 and upper jam washer 3 and also bearing rod 4 and push rod 18. The use of tubing for the rods would reduce the weight.

An alternative method of providing close calibration would be to provide bearing rod 4 with a series of circumferential grooves into which lower jam washer 2 and upper jam washer 3 would lock with each cycle. This would eliminate the chance of slippage or a random gripping.

Bearing rod 4 should have a cap 16 at its upper end to prevent upper jam washer 3 from falling off if the assembly is inverted. A similar cap 17 or enlargement should be part of push rod 18 so it will not fall out of the assembly when released. Cap 17 must be small enough so as not to interfere with lower jam washer 2 coming to rest nearly flat on upper bearing disc 8.

In operation for cycle counting of a lung exerciser, push rod 18 would be extended to reach inside the bellows of the unit so the bottom of the bellows would contact the push rod 18 as the bellows was emptied of air. Other activation systems such as using contact arms, buttons or integral push rods attached to the bellows could also be used. When nearly all the air was out of the bellows and it was collapsed sufficiently to call the cycle successfully completed, the push rod 18 would have been moved up enough to push lower jam washer 2 up into contact with upper jam washer 3. The patient using the exerciser would be able to see the goal had been reached and the cycle counted by observing the movement of upper jam washer 3 or the appearance over the end of tube 7 of cap 17 on push rod 18 which could be an easily detected color. When the prescribed number of cycles were completed, the unit could be reset back to zero by lifting upper jam washer 3 to a level position thereby allowing bearing rod 4 to fall back to the bottom rest position.

I claim:

1. A device to be used to register or count cycles of vertical motion as would occur when a bellows was being used for a volume breathing exercise needing a very light actuating force, said counter assembly consisting of:

a. a push rod for sensing cycles of vertical motion;

b. a bearing rod having an indicator disc at one end to serve as a moving indicator;

c. a thin walled transparent elongated tube closed at one end, said closed end having a guide hole therein positioned eccentrically to the longitudinal axis of said tube, said elongated tube having an open opposite end cut at an angle with respect to the longitudinal axis thereof, a bearing disc mounted in said tube adjacent said open end and having two guide holes therein, one of said guide holes being aligned with the guide hole in said closed end of said tube, the other guide hole being centrally positioned therein, said bearing rod having said indicator disc being slidably mounted in said tube with said indicator disc located between said closed end and said bearing disc and said bearing rod passing through said central guide hole in said bearing disc, said indicator disc having a guide hole therein in alignment with the guide hole in said closed end of said tube, said push rod being slidably mounted in said aligned guide holes in said closed end, said indicator disc and said bearing disc and being of sufficient length to extend from within said elongated tube, said tube having calibrated graduations on its side to correspond with alignment of the indicator disc;

d. a first plane circular disc having a hole at its center and mounted over said bearing rod between said bearing disc and said open end of said tube, said hole having a small clearance to the diameter of said bearing rod, said first disc being sized to fit inside said elongated tube and overlie said guide hole in said bearing disc;

e. a second plane circular disc having a hole at its center and mounted over said bearing rod adjacent the open end of said tube, said hole having a small clearance to the diameter of said bearing rod, said second disc being sized to contact with its outer edge the upper-most point of the angle cut of said elongated tube;

f. whereby, in response to reciprocating movement of said push rod against said first disc, said first and second discs provide an escapement or one way motion of the bearing rod with indicating disc by alternately gripping or releasing the bearing rod due to the push rod forcing the first disc to jam at an angle to the bearing rod and carry it up with the push rod a calibrated distance to the second disc which can only stop downward motion due to being forced to jam on the bearing rod by the angle cut of the open end of the tube;

g. wherein each completed cycle would lift the bearing rod with the first and second discs jammed on it above the edge of the angle cut of the open end of the tube indicating visually the end of a cycle; and h. said second disc constituting means to release the bearing rod with indicator disc by lifting the second disc back to a level position thereby allowing the bearing rod and indicator disc to drop and reset to zero.

2. The device of Claim One having adaptive means for attachment to an incentive spirometer that has a moving part that would reciprocate said push rod.

* * * * *